Jan. 8, 1957 W. A. LAW Plant Pat. 1,550
APPLE TREE
Filed Feb. 27, 1956
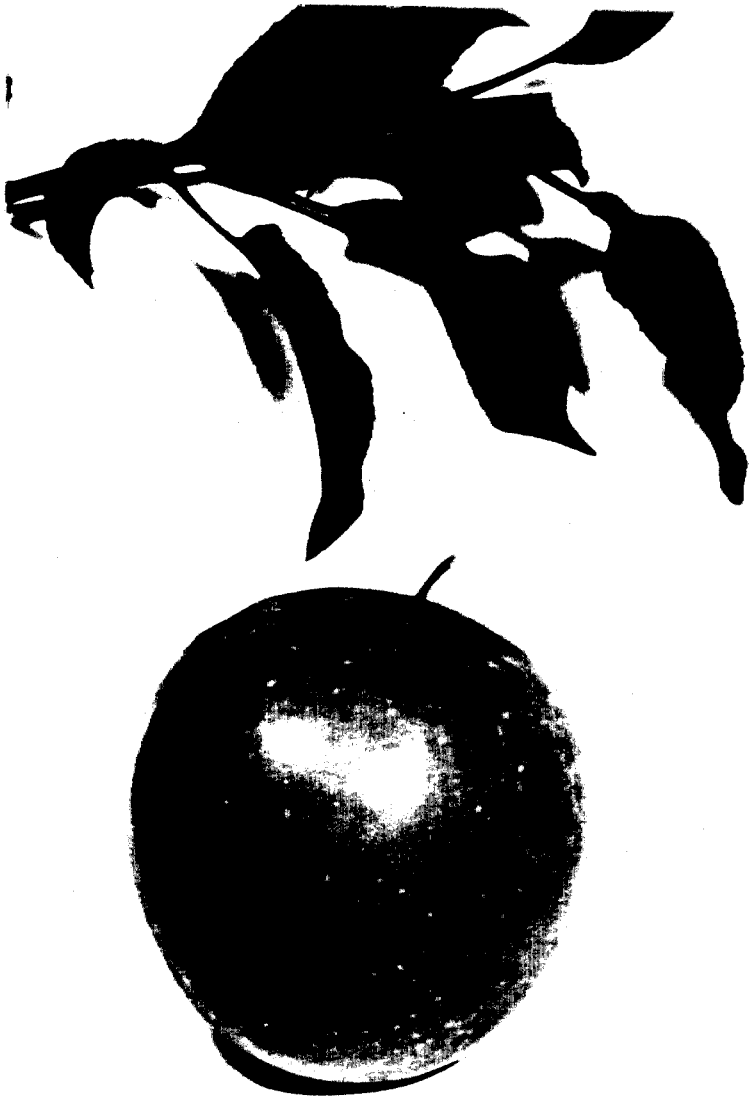
Inventor.
Walter A. Law
By: Robb & Robb
Attorneys United States Patent Office Plant Pat. 1,550
Patented Jan. 8, 1957

1,550

APPLE TREE

Walter A. Law, Tonasket, Wash., assignor to Stark Bro's Nurseries and Orchards Company, Louisiana, Mo., a corporation of Missouri Application February 27, 1956, Serial No. 568,133

1 Claim. (Cl. 47—62)

The present invention relates to a new and distinct variety of apple tree which was discovered by me as a bud sport of "Red Rome Beauty" (unpatented) in my cultivated orchard on my ranch at Tonasket, Okanogan County, Washington.

At the time of my discovery, my attention was attracted to a particular tree of "Red Rome Beauty" which appeared to be bearing fruit that was quite different from the normal fruit of this parent variety, such differences being evidenced by the larger size, longer and more conical shape of the fruit, and by their earlier, more uniform and brighter red color. Upon closer examination of the distinctively different fruit just mentioned, I found that the parent tree has apparently sported, and I thereupon promptly took steps to preserve and propagate the new sport.

Asexual reproduction by grafting, as performed on my behalf at Louisiana, Missouri, and continued observations and testing of the new sport have fully established that the distinctive characteristics aforementioned come true to form and are fixed and transmissible through succeeding propagations.

While my new variety more nearly resembles its parent "Red Rome Beauty" than any other variety, it is definitely distinguished therefrom, as well as from all other varieties of which I am aware, and the distinctive features thereof constitute substantial improvements over the parent variety and represent exceedingly desirable characteristics from a commercial standpoint.

The accompanying drawing shows typical specimens of the foliage and fruit of my new variety as depicted in color as nearly true as it is reasonably possible to make the same in a color illustration of this character.

The following is a detailed description of my new variety, with color terminology in accordance with Ridgway's Color Standards and Nomenclature and with the Horticultural Color Guide, as indicated, except where general color terms of ordinary dictionary significance are obvious:

Observations made from specimens grown in Okanogan County, Washington, and at Louisiana, Missouri.

Dates of first and last pickings: About October 23rd; can be harvested at one picking, which is a definite advantage from a commercial standpoint, although picking can be extended over several days.

Tree: Large; vigorous; upright; tall; vase-formed; hardy; rapid-growing; productive; regular bearing.

*Trunk.*—Medium stockiness; medium smoothness.

*Branches.*—Medium slender; smooth; much-branched.

*Twigs.*—Color—Claret Brown, Plate I, Color No. 5, Tone M (Ridgway).

*Lenticels.*—medium number; medium size.

*Leaves.*—Medium size; medium width (about 2⅛ inches); medium length (about 3¾ inches); oval; taper-pointed; medium thickness; smooth.

*Color.*—Spinach Green, Plate 0960/1, page 187, Vol. 2 (Horticultural Color Guide).

*Margin.*—Finely serrated.

*Petiole.*—Medium length (about 1⅛ inches); medium slender.

Flowers: Large; late as compared with other varieties, but substantially the same as "Rome Beauty."

*Color.*—White.

*Date of first bloom.*—About May 12th.

*Date of full bloom.*—About May 18th.

Fruit:

*Maturity when described.*—Eating ripe; about November 25th.

*Size.*—Uniform.

*Axial diameter.*—About 2⅝ inches.

*Transverse diameter.*—About 3 inches.

*Shape.*—Conical; truncate at base.

*Cavity.*—Symmetrical; flaring towards apex; even; pubescent towards apex.

*Depth.*—About 5/16 inch.

*Breadth.*—About 1⅛ inches.

*Basin.*—Symmetrical; rounded at base; wide; furrowed; pubescent.

*Depth.*—About ¼ inch.

*Breadth.*—About 1 inch.

*Stem.*—Clubbed; medium slender; pubescent.

*Length.*—About 1 inch.

*Breadth.*—About ⅛ inch.

*Calyx.*—Closed; segments persistent; narrowly lanceolate; acute; about 5/16 inch in length; calyx segments separated at base; ascending; converged from base towards center.

*Outer surface.*—Pubescent.

*Inner surface.*—Pubescent.

*Eye.*—Medium size; partially closed.

*Skin.*—Thick; tough; smooth; glossy; waxed.

*Dots.*—Obscure; many; small; depressed; circular. Color—Tilleul Buff, Plate XL, Color No. 17''', Tone F (Ridgway). Distribution—Over all; most numerous towards calyx end.

*Ground color.*—Uranium Green, Plate 663/3, page 90, Vol. 1 (Horticultural Color Guide).

*Color markings.*—Blushed; self-colored; bright. Color—Carmine, Plate I, Color No. 1, Tone i (Ridgway).

*Bloom.*—Wanting.

*Scarfskin.*—Wanting.

*General color effect.*—Deep solid Red.

*Flesh.*—Rather juicy.

*Color.*—Satiny White with greenish tint.

*Texture.*—Firm; fine; crisp.

*Flavor.*—Subacid.

*Aroma.*—Wanting.

*Quality.*—Good.

*Core.*—Median; large; distinct in cross section.

*Bundle area.*—Medium size; cordate; symmetrical; acute at base; in bundles opposite and alternate with cell.

*Halves of core.*—Equal.

*Bundles.*—Conspicuous; in one whorl. Color—Chartreuse Green, Plate 663/2, page 2 Vol. 1 (Horticultural Color Guide).

*Core lines.*—Just clasping.

*Calyx tube.*—Pubescent towards base; broadly obconic; entire depth about 5/16 inch.

*Styles.*—Present; fleshy at base; united towards base; pubescent at apex; glabrous towards base.

*Stamens.*—In one distinct whorl; median.

*Axillary cavity.*—Present.

*Seed cells.*—Axile; open. Cell walls—distant; thick; tough. Length—about ¾ inch. Breadth—about ⅜ inch. Longitudinal section—semi-orbicular; emarginate. Cross section—broad. Surface—fissured; smooth.

Seeds:

*Number.*—8 perfect; 1 imperfect; 2 per cell.

*Length.*—About ⅜ inch.

*Breadth.*—About 3/16 inch.

*Form.*—Acute.

*Color.*—Sorghum Brown, Plate XXXIX, Color 9''', Tone i (Ridgway).

Use: Market; culinary.

Keeping quality: Good; about 120 days in ordinary storage.

I claim:

A new and distinct variety of apple tree, substantially as herein shown and described, characterized particularly as to novelty by its general similarity to its parent variety "Red Rome Beauty" (unpatented), but being distinguished therefrom by the larger size of its fruit, the longer and more conical shape of its fruit, and the earlier, more uniform, all over bright Red coloring of its fruit.

No references cited